(12) United States Patent
Foerster et al.

(10) Patent No.: US 7,044,957 B2
(45) Date of Patent: May 16, 2006

(54) DEVICES FOR DEFINING AND MARKING TISSUE

(75) Inventors: Seth A. Foerster, San Clemente, CA (US); Fred H. Burbank, San Juan Capistrano, CA (US); Mark A. Ritchart, Murrieta, CA (US); Elias A. Zerhouni, Baltimore, MD (US)

(73) Assignee: Ethicon Endo-Surgery, Inc., Cinncinnati, OH (US)

( * ) Notice: Subject to any disclaimer, the term of this patent is extended or adjusted under 35 U.S.C. 154(b) by 276 days.

(21) Appl. No.: 09/776,125

(22) Filed: Feb. 2, 2001

(65) Prior Publication Data

US 2001/0034528 A1 Oct. 25, 2001

Related U.S. Application Data

(63) Continuation of application No. 08/858,389, filed on May 19, 1997, now Pat. No. 6,228,055, which is a continuation of application No. 08/308,097, filed on Sep. 16, 1994, now abandoned.

(51) Int. Cl.
*A61B 17/34* (2006.01)

(52) U.S. Cl. ...................................... 606/185
(58) Field of Classification Search ......... 606/181–185, 606/167, 116, 117; 600/562, 564, 431, 407, 600/420
See application file for complete search history.

(56) References Cited

U.S. PATENT DOCUMENTS 2,609,347 A 9/1952 Wilson
2,653,917 A 9/1953 Hammon (Continued)

FOREIGN PATENT DOCUMENTS

| DE | 0935625 | 11/1955 |
|---|---|---|
| DE | 4330958 | 3/1995 |
| DE | 4403789 | 8/1995 |
| EP | 0 146 699 A1 | 7/1985 |
| EP | 0255123 | 2/1988 |
| EP | 0 481 685 A1 | 4/1992 |
| EP | 0 350 043 B1 | 8/1992 |
| EP | 0 293 605 B1 | 8/1993 |
| EP | 0769281 | 4/1997 |
| EP | 0 894 503 A2 | 8/1998 |
| FR | 2714284 | 9/1995 |
| GB | 2 132 091 A | 7/1984 |
| GB | 2132091 | 7/1984 |
| JP | 9-66063 A | 3/1997 |
| WO | 90/15576 A1 | 12/1990 |
| WO | 93/19803 A1 | 10/1993 |
| WO | WO 95/13746 | 5/1995 |
| WO | WO 96/08208 | 9/1996 |
| WO | WO 98/09247 A1 | 3/1998 |
| WO | WO 98/10712 | 3/1998 |
| WO | WO 98/47430 | 10/1998 |
| WO | WO 98/52617 A2 | 11/1998 |
| WO | WO 99/25248 A1 | 5/1999 |
| WO | WO 99/46284 A2 | 9/1999 |
| WO | 00/38579 A2 | 12/1999 |
| WO | WO 00/24320 A1 | 5/2000 |
| WO | WO 00/78228 A1 | 12/2000 |

OTHER PUBLICATIONS

Parker and Klaus; From the RSNA Refresher Courses: Performing a Breast Biopsy With Directional, Vacuum–assisted Biopsy Instrument; Radiographics vol. 17/5, 1997, pp 1233–1252.

(Continued)

*Primary Examiner*—Anhtuan T. Nguyen
*Assistant Examiner*—Jessica R. Baxter

(57) ABSTRACT

In order to later identify the location of a biopsy or surgery, various means and methods for permanently and non-surgically marking selected tissue in the human body are used. Later visualization of the markers is readily accomplished using state-of-the-art imaging systems.

15 Claims, 7 Drawing Sheets

U.S. PATENT DOCUMENTS

| | | |
|---|---|---|
| 2,659,935 A | 11/1953 | Hammon |
| 2,664,366 A | 12/1953 | Wilson |
| 2,664,367 A | 12/1953 | Wilson |
| 2,846,407 A | 8/1958 | Wilson |
| 3,001,522 A | 9/1961 | Silverman |
| 3,120,230 A | 2/1964 | Skold |
| 3,194,239 A | 7/1965 | Sullivan |
| 3,592,185 A | 7/1971 | Ephraim et al. |
| 3,823,212 A | 7/1974 | Chvapi |
| 3,945,375 A | 3/1976 | Banko |
| 3,958,576 A | 5/1976 | Komiya |
| 3,996,935 A | 12/1976 | Banko |
| 4,080,959 A | 3/1978 | Leveen |
| 4,086,914 A * | 5/1978 | Moore ............... 604/64 |
| 4,087,791 A | 5/1978 | Lemberger |
| 4,103,690 A | 8/1978 | Harris |
| 4,103,692 A | 8/1978 | Baier et al. |
| 4,197,846 A | 4/1980 | Bucalo |
| 4,210,146 A | 7/1980 | Banko |
| 4,230,123 A | 10/1980 | Hawkins |
| 4,247,406 A | 1/1981 | Widder et al. |
| 4,248,214 A | 2/1981 | Hannah et al. |
| 4,250,892 A | 2/1981 | Dolhay et al. |
| 4,298,998 A | 11/1981 | Naficy |
| 4,320,761 A | 3/1982 | Haddad |
| 4,347,234 A | 8/1982 | Wahlig et al. |
| 4,365,572 A | 12/1982 | Stevenson, IV |
| 4,402,308 A * | 9/1983 | Scott ............... 604/60 |
| 4,511,653 A | 4/1985 | Play et al. |
| 4,541,438 A | 9/1985 | Parker et al. |
| 4,583,538 A | 4/1986 | Onik et al. |
| 4,592,356 A | 6/1986 | Gutierrez |
| 4,649,151 A | 3/1987 | Dougherty et al. |
| 4,682,606 A | 7/1987 | DeCaprio |
| 4,693,237 A | 9/1987 | Hoffman et al. |
| 4,699,154 A | 10/1987 | Lindgren |
| 4,703,108 A | 10/1987 | Silver et al. |
| 4,709,703 A * | 12/1987 | Lazarow et al. ............ 600/508 |
| 4,718,897 A | 1/1988 | Elves |
| 4,733,664 A | 3/1988 | Kirsch et al. |
| 4,735,210 A | 4/1988 | Goldenberg |
| 4,735,796 A | 4/1988 | Gordon |
| 4,774,948 A | 10/1988 | Markham |
| 4,787,391 A | 11/1988 | Elefteriades |
| 4,799,495 A | 1/1989 | Hawkins et al. |
| 4,813,422 A | 3/1989 | Fisher et al. |
| 4,817,622 A | 4/1989 | Pennypacker et al. |
| 4,832,685 A | 5/1989 | Haines |
| 4,832,686 A | 5/1989 | Anderson |
| 4,852,568 A | 8/1989 | Kensey |
| 4,853,210 A | 8/1989 | Kass |
| 4,871,094 A * | 10/1989 | Gall et al. ............ 604/59 |
| 4,881,551 A | 11/1989 | Taylor |
| 4,900,304 A * | 2/1990 | Fujioka et al. ............ 604/60 |
| 4,907,599 A | 3/1990 | Taylor |
| 4,909,250 A | 3/1990 | Smith |
| 4,929,240 A | 5/1990 | Kirsch et al. |
| 4,935,005 A | 6/1990 | Haines |
| 4,944,308 A | 7/1990 | Akerfeldt |
| 4,966,583 A | 10/1990 | Debbas |
| 4,970,298 A | 11/1990 | Silver |
| 4,986,279 A | 1/1991 | O'Neill |
| 4,994,013 A * | 2/1991 | Suthanthiran et al. ......... 600/8 |
| 4,994,069 A | 2/1991 | Ritchart et al. |
| 4,995,877 A | 2/1991 | Ams et al. |
| 5,002,548 A | 3/1991 | Campbell et al. |
| 5,014,713 A | 5/1991 | Roper et al. |
| 5,018,530 A | 5/1991 | Rank et al. |
| 5,024,727 A | 6/1991 | Campbell et al. |
| 5,025,797 A | 6/1991 | Baran |
| 5,041,826 A | 8/1991 | Milheiser |
| 5,061,281 A | 10/1991 | Mares et al. |
| 5,080,655 A | 1/1992 | Haaga |
| 5,083,570 A | 1/1992 | Mosby |
| 5,085,629 A | 2/1992 | Golberg et al. |
| 5,101,827 A | 4/1992 | Goldenberg |
| 5,108,407 A | 4/1992 | Geremia et al. |
| 5,108,421 A | 4/1992 | Fowler |
| 5,112,299 A | 5/1992 | Pascaloff |
| 5,114,703 A | 5/1992 | Wolf et al. |
| 5,120,802 A | 6/1992 | Mares et al. |
| 5,122,147 A | 6/1992 | Sewell |
| 5,125,413 A | 6/1992 | Baran |
| 5,127,916 A | 7/1992 | Spencer et al. |
| 5,133,661 A | 7/1992 | Euvrard |
| 5,147,307 A | 9/1992 | Gluck |
| 5,148,813 A | 9/1992 | Bucalo |
| 5,156,609 A | 10/1992 | Nakao et al. |
| 5,158,084 A | 10/1992 | Ghiatas |
| 5,158,565 A | 10/1992 | Marcadis et al. |
| 5,188,111 A | 2/1993 | Yates et al. |
| 5,192,270 A | 3/1993 | Carswell, Jr. |
| 5,192,292 A | 3/1993 | Cezana et al. |
| 5,192,300 A | 3/1993 | Fowler |
| 5,195,540 A | 3/1993 | Shiber |
| 5,195,988 A | 3/1993 | Haaga |
| 5,197,482 A | 3/1993 | Rank et al. |
| 5,201,314 A | 4/1993 | Bosley et al. |
| 5,204,382 A | 4/1993 | Wallace |
| 5,207,705 A | 5/1993 | Trudell |
| 5,209,232 A | 5/1993 | Levene |
| 5,217,478 A | 6/1993 | Rexroth |
| 5,221,269 A | 6/1993 | Miller et al. |
| 5,226,911 A | 7/1993 | Chee et al. |
| 5,234,426 A | 8/1993 | Rank et al. |
| 5,242,456 A | 9/1993 | Nash et al. |
| 5,242,457 A | 9/1993 | Akopov et al. |
| 5,274,074 A | 12/1993 | Tang et al. |
| 5,275,609 A | 1/1994 | Pingleton et al. |
| 5,280,457 A | 1/1994 | Figueroa et al. |
| 5,300,120 A | 4/1994 | Knapp et al. |
| 5,320,635 A | 6/1994 | Smith |
| 5,325,857 A | 7/1994 | Nabai et al. |
| 5,326,350 A | 7/1994 | Li |
| 5,334,216 A | 8/1994 | Vidal et al. |
| 5,342,283 A | 8/1994 | Good |
| 5,353,804 A | 10/1994 | Kornberg et al. |
| 5,358,474 A * | 10/1994 | Kaldany ............... 606/170 |
| 5,364,406 A | 11/1994 | Sewell, Jr. |
| 5,388,588 A | 2/1995 | Nabai et al. |
| 5,394,886 A | 3/1995 | Nabai et al. |
| 5,395,319 A | 3/1995 | Hirsch et al. |
| 5,400,798 A | 3/1995 | Baran |
| 5,403,276 A | 4/1995 | Schechter et al. |
| 5,409,004 A | 4/1995 | Sloan |
| RE34,936 E | 5/1995 | Campbell et al. |
| 5,411,522 A | 5/1995 | Trott |
| 5,413,584 A | 5/1995 | Schulze |
| 5,423,321 A | 6/1995 | Fontenot |
| 5,433,751 A | 7/1995 | Christel et al. |
| 5,437,279 A | 8/1995 | Gray |
| 5,445,167 A | 8/1995 | Yoon et al. |
| 5,467,780 A | 11/1995 | Nabai et al. |
| 5,469,854 A | 11/1995 | Unger et al. |
| 5,470,308 A | 11/1995 | Edwards et al. |
| 5,479,936 A | 1/1996 | Nabai et al. |
| 5,482,040 A | 1/1996 | Martin, Jr. |
| 5,483,972 A | 1/1996 | Nabai et al. |
| 5,487,392 A * | 1/1996 | Haaga ............... 600/566 |
| 5,496,314 A | 3/1996 | Eggers |
| 5,496,536 A | 3/1996 | Wolf |

| | | | |
|---|---|---|---|
| 5,507,813 A | | 4/1996 | Dowd |
| 5,514,379 A | | 5/1996 | Weissleder et al. |
| 5,517,997 A | | 5/1996 | Fontenot |
| 5,522,896 A | | 6/1996 | Prescott |
| 5,526,822 A | * | 6/1996 | Burbank et al. ............ 600/567 |
| 5,538,010 A | * | 7/1996 | Darr et al. .................. 600/567 |
| 5,555,885 A | | 9/1996 | Chance |
| 5,556,410 A | | 9/1996 | Mittermeir et al. |
| 5,562,613 A | * | 10/1996 | Kaldany ..................... 606/170 |
| 5,571,182 A | | 11/1996 | Ersek et al. |
| RE35,391 E | | 12/1996 | Brauman |
| 5,579,766 A | | 12/1996 | Gray |
| 5,582,172 A | | 12/1996 | Papisov et al. |
| 5,595,177 A | | 1/1997 | Mena et al. |
| 5,626,611 A | | 5/1997 | Liu et al. |
| 5,645,566 A | | 7/1997 | Brenneman |
| 5,647,374 A | | 7/1997 | Cutrer |
| 5,649,547 A | * | 7/1997 | Ritchart et al. ............ 600/566 |
| 5,660,185 A | | 8/1997 | Shmulewitz et al. |
| 5,670,161 A | | 9/1997 | Brenneman |
| 5,674,288 A | | 10/1997 | Knapp et al. |
| 5,676,146 A | | 10/1997 | Scarborough |
| 5,676,146 A | | 10/1997 | Scarborough |
| 5,681,262 A | | 10/1997 | Isse |
| 5,697,902 A | | 12/1997 | Goldenberg |
| 5,716,404 A | | 2/1998 | Vacanti |
| 5,716,407 A | | 2/1998 | Knapp et al. |
| 5,718,237 A | | 2/1998 | Haaga |
| 5,725,578 A | | 3/1998 | Knapp et al. |
| 5,732,704 A | | 3/1998 | Thurston et al. |
| 5,752,974 A | | 5/1998 | Rhee |
| 5,776,093 A | | 7/1998 | Goldenberg |
| 5,776,094 A | | 7/1998 | Goldenberg |
| 5,795,308 A | | 8/1998 | Russin |
| 5,803,913 A | | 9/1998 | Khalkhali et al. |
| 5,807,276 A | | 9/1998 | Russin |
| 5,810,806 A | | 9/1998 | Ritchart et al. |
| 5,824,081 A | | 10/1998 | Knapp et al. |
| 5,855,609 A | | 1/1999 | Knapp |
| 5,857,463 A | | 1/1999 | Thurston et al. |
| 5,868,778 A | | 2/1999 | Gershony et al. |
| 5,869,080 A | | 2/1999 | McGregor et al. |
| 5,873,904 A | | 2/1999 | Ragheb et al. |
| 5,879,357 A | * | 3/1999 | Heaton et al. ............. 606/116 |
| 5,895,640 A | | 4/1999 | Khalkhali |
| 5,899,865 A | | 5/1999 | Chance |
| 5,902,310 A | | 5/1999 | Foerster et al. |
| 5,913,857 A | | 6/1999 | Ritchart et al. |
| 5,922,024 A | | 7/1999 | Janzen et al. |
| 5,941,910 A | | 8/1999 | Schindler |
| 5,970,986 A | | 10/1999 | Bolz et al. |
| 5,977,431 A | | 11/1999 | Knapp et al. |
| 5,980,564 A | | 11/1999 | Stinson |
| 6,053,876 A | | 4/2000 | Fisher |
| 6,053,925 A | | 4/2000 | Barnhart |
| 6,056,700 A | * | 5/2000 | Burney et al. .............. 606/167 |
| 6,066,325 A | | 5/2000 | Wallace et al. |
| 6,071,301 A | | 6/2000 | Cragg et al. |
| 6,161,034 A | | 12/2000 | Burbank et al. |
| 6,162,192 A | | 12/2000 | Cragg |
| 6,174,330 B1 | | 1/2001 | Stinson |
| 6,183,497 B1 | | 2/2001 | Sing et al. |
| 6,214,045 B1 | | 4/2001 | Corbitt, Jr. et al. |
| 6,228,055 B1 | * | 5/2001 | Foerster et al. ............ 606/185 |
| 6,231,834 B1 | | 5/2001 | Unger et al. |
| 6,234,177 B1 | * | 5/2001 | Barsch ....................... 606/116 |
| 6,258,070 B1 | * | 7/2001 | Kaldany ..................... 604/60 |
| 6,270,464 B1 | | 8/2001 | Fulton et al. |
| 6,271,278 B1 | | 8/2001 | Park et al. |
| 6,335,028 B1 | | 1/2002 | Vogel et al. |
| 6,347,241 B1 | | 2/2002 | Burbank et al. |
| 6,350,244 B1 | * | 2/2002 | Fisher ........................ 606/116 |
| 6,356,782 B1 | | 3/2002 | Sirimanne et al. |
| 6,371,904 B1 | | 4/2002 | Sirimanne |
| 2001/0023322 A1 | | 9/2001 | Esposito et al. |
| 2001/0034528 A1 | | 10/2001 | Foerster et al. |
| 2004/0024304 A1 | | 2/2004 | Foerster et al. |

OTHER PUBLICATIONS

Leonard et al.; Use of Ultrasound to Guide Radiation Boost Planning Following Lumpectomy for Carcinoma of the Breast; Int. Journal Radiation Oncology, vol. 27, 1993, pp 1193–1197.

Thomson et al.; Stereotacic Brain Biopsy Using a Narrow Aperture Computed Tomography Scanner; Clinical Radiology, vol 35, 1984, pp 209–214.

Seoudi et al; Stereotactic Core Needle Biopsy of Nonpalpable Breast Lesions– Initial Experience With a Promising Technique; Arch. Surgery; vol. 133, Apr. 1988; pp 366–372.

Hofmann et al.; Biodegradable Implants in Orthopaedic Surgery—A Review on the State–of–the–Art; Clinical Materials; vol. 10, 1992; pp 75–80.

Parker and Burbank; A Practical Approach to Minimally Invasive Breast Biopsy; Radiology; vol 200, 1996, pp 11–20.

Letters; Letters to the American Journal of Radiology; AJR vol. 164, Jan. 1995, pp 260–261.

Lee and Knochel; Technical Developments and Instrumentation: Air as an Ultrasound Contrast Marker for Accurate Determination of Needle Placement; Radiology 143; Jun. 1982; pp.787–788.

Sullivan; Perspective: Needle Core Biopsy of Mammographic Lesions; AJR vol 162, Mar. 1994 (received Sep. 20, 1993) pp 601–608.

Yandow and Matallana; Gas Contrast Guided Needle Biopsy of the Head of the Pancreas; Radiology vol. 137, Nov. 1980; pp 543–544.

Lee et al.; Air as a Contrast Marker for Ultrasound–Guided Fetal Transfusions; Radiology, vol 138, Feb. 1981, pp 490–491.

EPO Search Report dated Dec. 5, 2003 for EPO Application No. EP 03 07 5084.

Hussman et al., "Optical Breast Lesion Localization Fiber: Preclinical Testing of a New Device," Radiology, 200:865–866 (Sep. 1996).

Hussman et al., "MR Mammographic Localization Work in Progress," Radiology, 189:915–917 (1993).

"Surgical Treatment of Breast Disease, Making the Diagnosis of Breast Cancer: Non–Palpable Breast Masses," BreastDoctor.com, http://www.breastdoctor.com/breast/surgery/biopsy.htm.

"Surgical Treatment of Breast Disease: What's New? Diagnosing Breast Cancer The ABBI Breast Biopsy System, "BreastDoctor.com, http://breastdoctor.com/breast/surgery/abbi.htm.

Fournier et al: "Experimental Studies and Preliminary Clinical Trial of Vinorelbine–loaded Polymeric Bioresorbable Implants for the Local Treatment of Solid Tumors," Cancer Research 51, pp., 5384–5391, Oct. 1, 1991.

Clarkson, P.: "Sponge Implants for Flat Breasts," Proceedings of the Royal Society of Medicine, vol. 53 at 880–881 (1960).

EPO search report dated Dec. 5, 2003, for EP03075084.8.

Pangman, W.J. and Wallace, R.M.: "The Use of Plastic Prothesis in Breast Plastic and Other Soft Tissue Surgery," The Western Journal of Surgery, Obstetrics and Gynecology at 508 (Aug. 1955).

Wang Hom–Lay et al. "Evalution of an Absorable Collagen Membrane in Treating Class II Furcation Defects", pp. 1029–1036. Nov. 1994.

Brophy M. Regina et al. "Biodegradable Polyester Polymers as Drug Carriers", pp. 1–25.

Swarbrick James and Boylan James. "Bioabsorbable Polymers," *The Encyclopedia of Pharmaceutical Technology*, vol. 1. Absorption of Drugs to Bioabilability of Drugs and Bioequivalence, New York and Basel. pp. 485–476.

Park, Kinam; Shalaby, Waleed and Park Haesun. "Biodegradable Hydrogels for Drug Delivery," *Purdue University School of Pharmacy*.pp. 13–19.

Tschakaloff A. et al. "Degradation Kinetics of Biodegradable Implants depending on the site of implantation," *Int, Journal of Oral & Maxilofacial Surgery*,1994. pp. 443–445.

Vert, Michel. Mauduit, Jacques and Li, Suming. "Biodegradation of PLA/GA Polymers increasing complexity," *Biomaterials* 1994 vol. 15. No. 15. pp. 1209–1213.

Hoffman, G.O. "Biodegradable Implants in Traumatology A Review on the State–of–the Art," *Arch Cathop Trauma Surgery,* 1995 pp. 114: 123–132.

Bostman. O. and Pihlajamaki, H. "Clinical Biocompatibility of Biodegradable Orthopaedic Implants for Internal Fixation," *Biomaterials*21 (2000) pp. 2615–2621.

Alonso, Maria J., Gupta. Rajesh K. et al. "Biodegradable Microspheres as Controlled–Release Tetanus Toxoid Delivery Systems," Vaccine 1994 vol. 12 No.4. pp. 299–304.

An, Yuehuei H., Woolf, Shane K., Friedman, Richard, "Preclinical in Vivo Evaluation of Orthopaedic Bioabsorbable Devices," *Biomaterials* 21 (2000) pp. 2635–2652.

Mooney, D.J. et al. "Transplantation of Hepalocytes Using Porous. Biodegradable Sponges." Transplantation Proceedings, vol. 28, No. 6 Dec. 1994 pp. 3425–3426.

Cutright, Duane E. et al. "Degradation Rates of Polymers and Copolymers of Polylactic and Polyglycolic Acids," U.S. Army Institute of Dantal Research, Walter Reed Army Medical Center, Washington, D.C. pp. 142–151.

Kulkarni, R. K. Phd. et al.: "Polyactic Acid for Surgical Implants," Arch Surgery. vol. 93, vol. 93, Nov. 1966 pp. 839–843.

Kulkarni, R. K. Phd. et al.: "Biodegradable Poly(lactic acid) Polymers," U.S. Army Institute of Dental Research, Walter Reed Army Medical Center, Washington, D.C. (1971) vol. 5, pp. 169–181.

Chasin, Mark and Langer, Robert, Lewis, Danny H. "Biodegradable Polymers as Drug Delivery Systems," Controlled Release of Bioactive Agents from Lactide/Glycolide Polymers Ch. 1 pp. 41 (1990). And Bogdanshy, Simon "Natural Polymers as Drug Delivery Systems." pp. 231–259.

Huang, Samuel J. et al.; Hydrophilic–Hydrophobic Biodegradable Polymers: Release characteristics of Hydrogen–Bonded, Ring–Containing Polymer Matrices. (1994) Biomaterials (1994), vol. 15 No. 15 pp. 1243–1247.

Becker, Paul L. "Comparsion of Antibiotic Release from Polymethlmetharylate Beads and Sponge Collagen." *Journal of Orthopaedic Research.* (1994) vol. 12, No. 5.

Mackinnon, Susan E. "Clinical Nerve Reconstruction with a Bioabsorbable Polyglycolic Acid Tube." *Plastic and Reconstructive Surgery,* Mar. 1990.

Nakamura. T., et al. "New Bioabsorbable Pledgets and Non–Woven Fabrics Made from Polyglycolide (PGA) for Pulmonary Surgery: Clinical Experience." *Thoracic Cardiovascular Surgeons*.(1990) pp. 81–85.

Tong, Xiao–Jie, et al.; "Sciatic Nerve Regeneration Navigated by Laminin–Fibronectin Double Coated Biodegradable Collagen Grafts in Rats." *Brain Research 663* (1994) pp. 155–162.

Matsusue, Yoshitaka, et al.: "In Vitro and In Vivo Studies on Bioabsorbable Ultra–High–Strength Poly (L–Lactide) Rods." Journal of Biomedical Materials Research (1992) vol. 28, pp. 1553–1567.

Hutmacher, Dietmar. "A Review of Material Properties of Biodegradable and Bioresorbable Polymers and Devices for GTR and GBR Applications." The International Journal of Oral & Maxillofacial Implants. (1996) vol. 11 No. 5. pp. 667–678.

Park, Kinam et al.; "Biodegradable Hydrogels for Drug Delivery." Purdue University, School of Pharmacy. pp. 2–28.

Chu. C.C. and Dumitriu, Severian *Polymeric Biomaterials $2^{nd}$ ed.* "Biodegradable Biomaterials Having Nitric Oxide Biological Activity." Ch. 5. pp. 123–124. and Rokkanen, Penttiu. Bioabsorbable Polymers for Medical Applications with an Emphasis on Orthopedic Sugery. Ch. 20 pp. 545–547.

Middleton, John C. and Tipton, Arthur.; "Synthetic Biodegradable Polymers as Medical Devices." (Mar. 1998) pp. 1–14 of website: http://www.devicelink.com/mph/archive/98/03/002.html. Aug. 28, 2002.

Tsuruta, Teiji; Kimura, Yoshibaru et al. "Biomedical Applications of Polymeric Materials." 1993 pp. 164–186.

Parker, Steve H. and Klaus, Anita J. "Performing a Breast Biopsy with A Directional, Vacuum–Assisted Biopsy Instrument," *From the RSNA Refresher Courses–Continuing Education* (1997) vol. 17 No. 5 pp. 1233–1252.

Leonard, Charles MD. et al. "Use of Ultrasound to Guide Radiation Boost Planning Following Lumpectomy for Carcinoma of The Breast." (Aug. 1993) *Interantional Radiation Oncology Biology. Phys.* vol. 27. pp. 1193–1197.

S.S. Kramer, et al., "A Permanent Radiopaque Marker Technique for the Study of Pharyngeal Swallowing in Dogs", *Dypshagia* (1987) pp. 163–167.

Homer, et al., "The Geographic Cluster of Microcalcifications of the Breast", *Surgery, Gynecology & Obstetrics* (1985).

Finan, et al., "Interstitial Radiotherapy for Early Stage Vaginal Cancer", *The Journal of Reproductive Medicine* (1993) vol. 38, No. 3.

Dufrane, P. et al., "Prebiopsy Localization of Non–Palpable Breast Cancer", *Journal Belgede Radiologie*(Oct. 1, 1990) vol. 73, No. 5.

\* cited by examiner

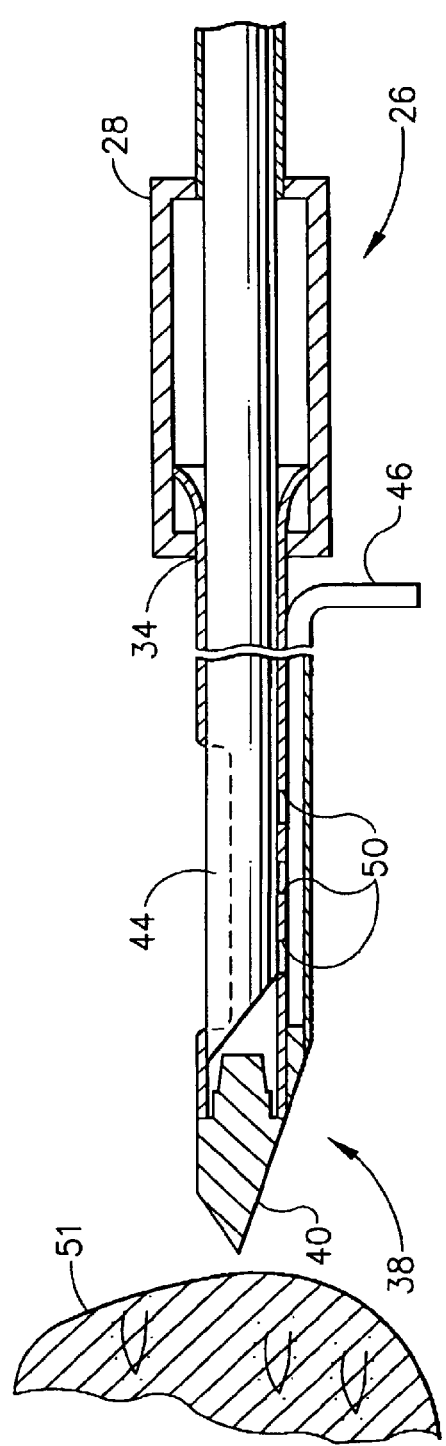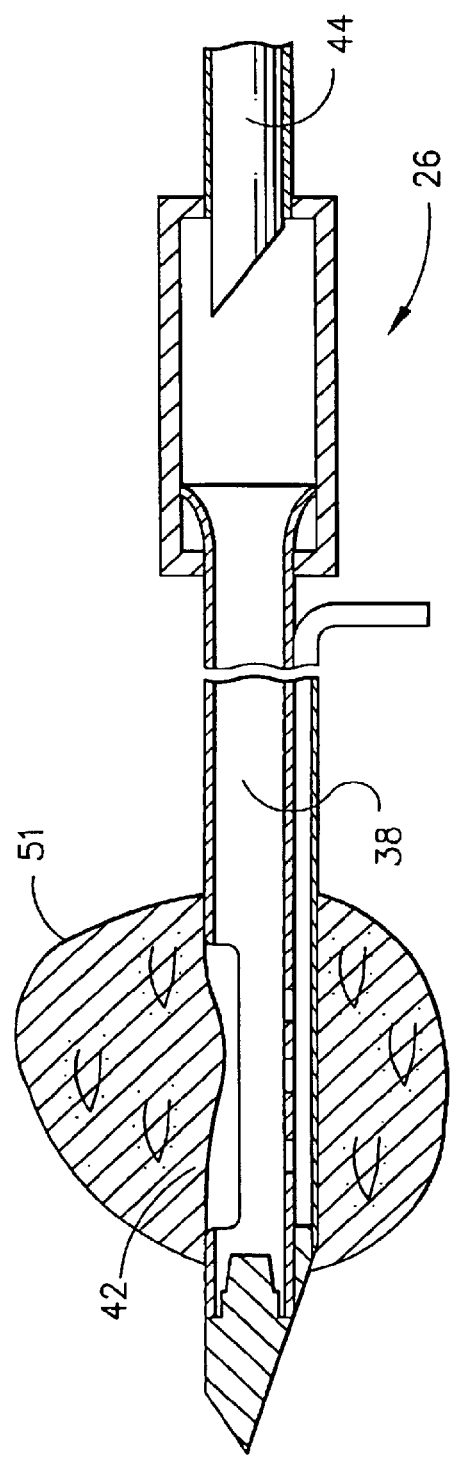

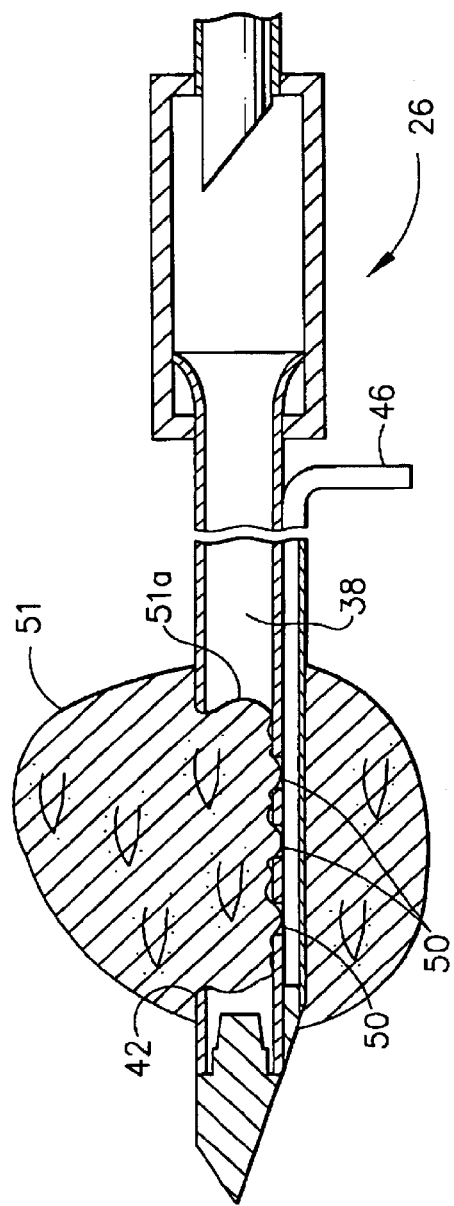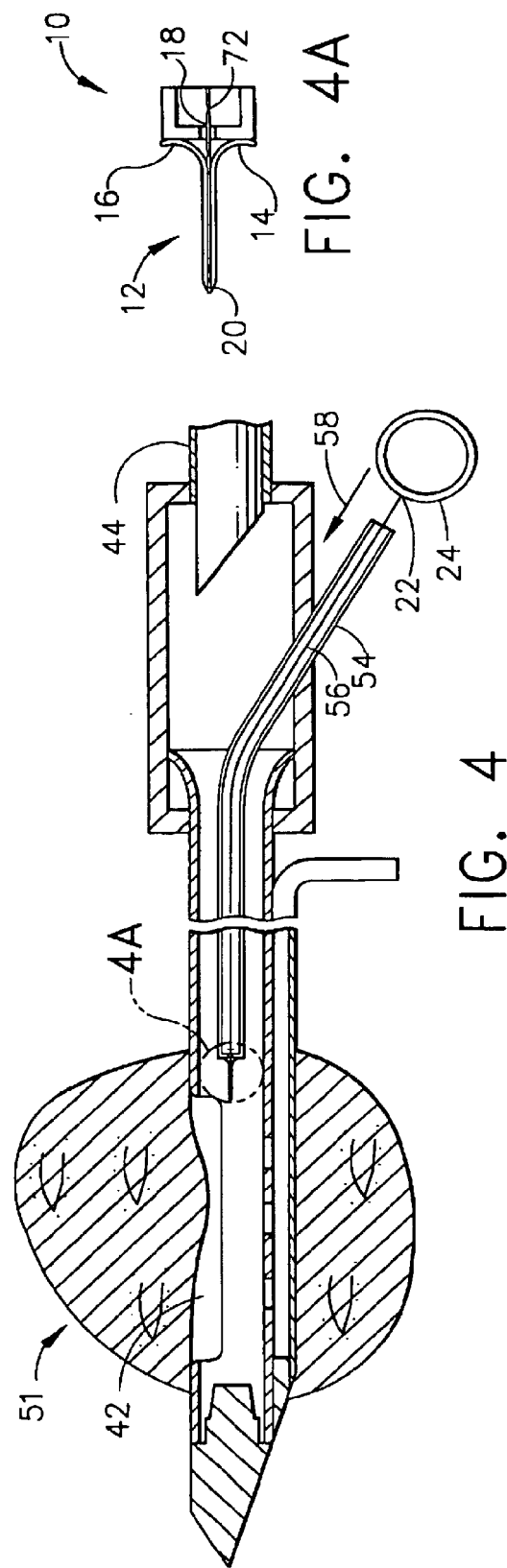
FIG. 3
FIG. 4
FIG. 4A

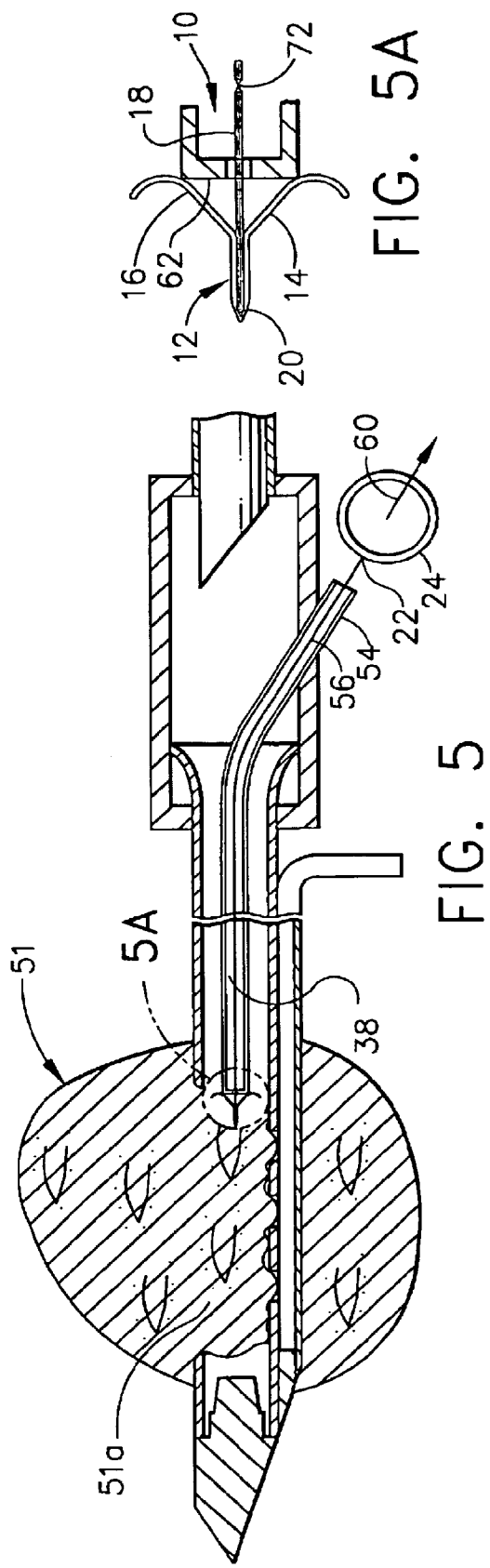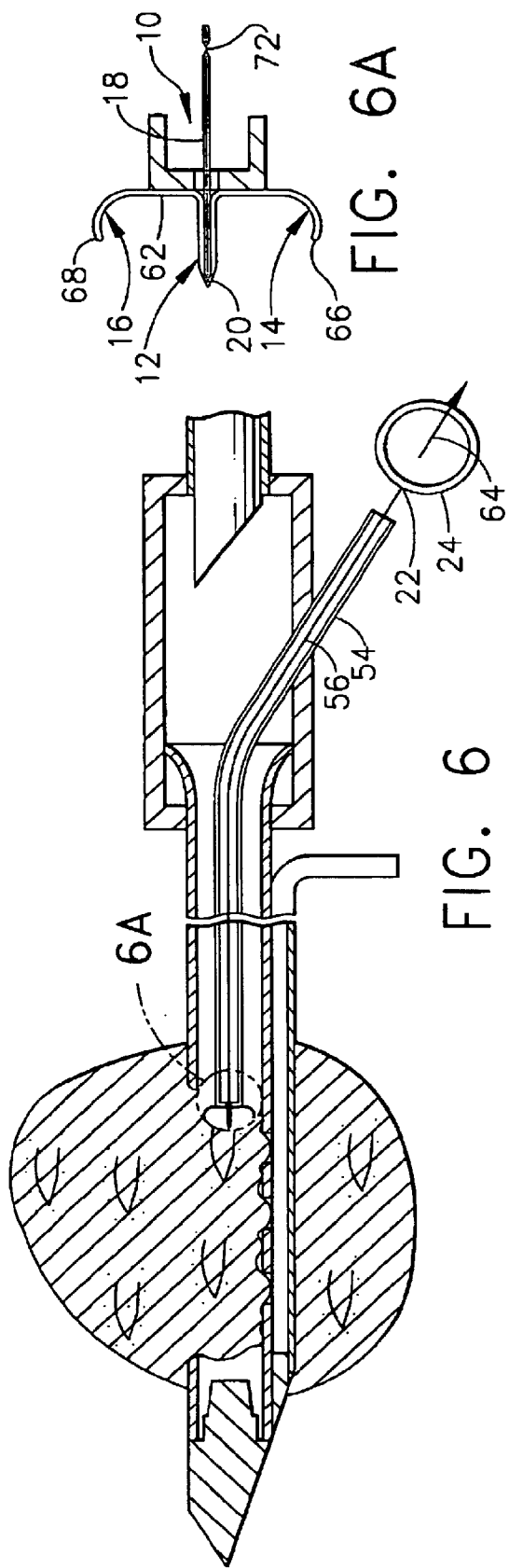

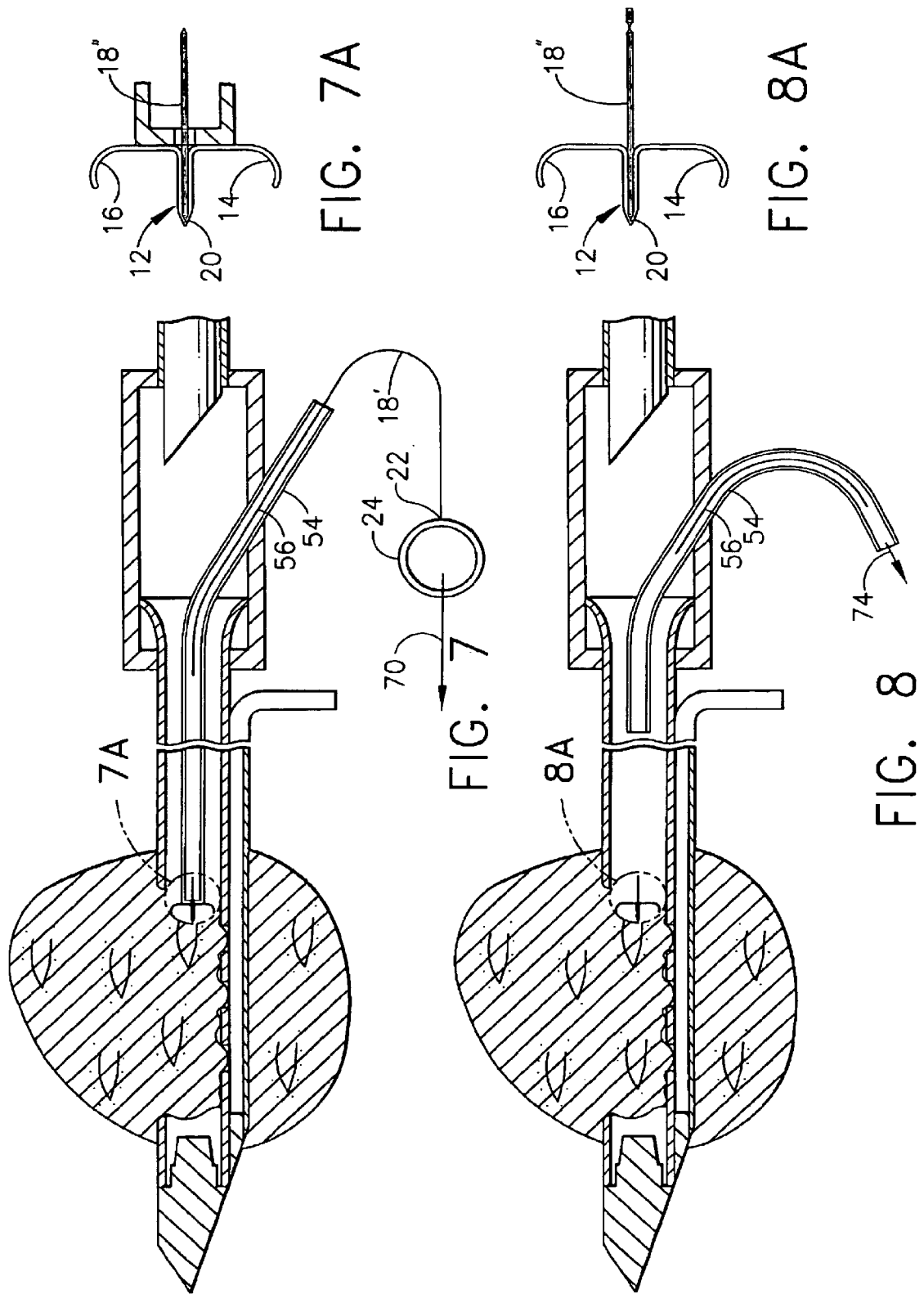

DEVICES FOR DEFINING AND MARKING TISSUE

This is a Continuation of Ser. No. 08/858,389 Filed May 19, 1997 now U.S. Pat. No. 6,228,055, which is a continuation of Ser. No. 08/308,097 Filed Sep. 16, 1994 now abandoned.

BACKGROUND OF THE INVENTION

This invention relates to methods and devices for marking and defining particular locations in human tissue, and more particularly relates to methods and devices for permanently defining the location and margins of lesions detected in a human breast.

It is desirable and often necessary to perform procedures for detecting, sampling, and testing lesions and other abnormalities in the tissue of humans and other animals, particularly in the diagnosis and treatment of patients with cancerous tumors, pre-malignant conditions and other diseases or disorders. Typically, in the case of cancer, when a physician establishes by means of known procedures (i.e. palpation, x-ray, MRI, or ultrasound imaging) that suspicious circumstances exist, a biopsy is performed to determine whether the cells are cancerous. Biopsy may be an open or percutaneous technique. Open biopsy removes the entire mass (excisional biopsy) or a part of the mass (incisional biopsy). Percutaneous biopsy on the other hand is usually done with a needle-like instrument and may be either a fine needle aspiration (FNA) or a core biopsy. In FNA biopsy, very small needles are used to obtain individual cells or clusters of cells for cytologic examination. The cells may be prepared such as in a Papanicolaou (Pap) smear. In core biopsy, as the term suggests, a core or fragment of tissue is obtained for histologic examination which may be done via a frozen section or paraffin section. The chief difference between FNA and core biopsy is the size of the tissue sample taken. A real time or near real time imaging system having stereoscopic capabilities, such as the stereotactic guidance system described in U.S. Pat. No. 5,240,011, is employed to guide the extraction instrument to the lesion. Advantageous methods and devices for performing core biopsies are described in the assignee's co-pending patent application Ser. No. 08/217,246, filed on Mar. 24, 1994, and herein incorporated by reference.

Depending upon the procedure being performed, it is sometimes desirable to completely remove suspicious lesions for evaluation, while in other instances it may be desirable to remove only a sample from the lesion. In the former case, a major problem is the ability to define the margins of the lesions at all times during the extraction process. Visibility of the lesion by the imaging system may be hampered because of the distortion created by the extraction process itself as well as associated bleeding in the surrounding tissues. Although the lesion is removed and all fluids are continuously aspirated from the extraction site, it is likely that the process will "cloud" the lesion, thus impairing exact recognition of its margins. This makes it difficult to ensure that the entire lesion will be removed.

Often, the lesion is merely a calcification derived from dead abnormal tissue, which may be cancerous or precancerous, and it is desirable to remove only a sample of the lesion, rather than the entire lesion, to evaluate it. This is because such a lesion actually serves to mark or define the location of adjacent abnormal tissue, so the physician does not wish to remove the entire lesion and thereby lose a critical means for later re-locating the affected tissue. One of the benefits to the patient from core biopsy is that the mass of the tissue taken is small. However, oftentimes, either inadvertently or because the lesion is too small, the entire lesion is removed for evaluation, even though it is desired to remove only a portion. Then, if subsequent analysis indicates the tissue to be malignant (malignant tissue requires removal, days or weeks later, of tissue around the immediate site of the original biopsy), it is difficult for the physician to determine the precise location of the lesion, in order to perform necessary additional procedures on adjacent potentially cancerous tissue. Additionally, even if the lesion is found to be benign, there will be no evidence of its location during future examinations, to mark the location of the previously removed calcification so that the affected tissue may be carefully monitored for future reoccurrences.

Thus, it would be of considerable benefit to be able to permanently mark the location or margins of such a lesion prior to or immediately after removing or sampling same. Marking prior to removal would help to ensure that the entire lesion is excised, if desired. Alternatively, if the lesion were inadvertently removed in its entirety, marking the biopsy site immediately after the procedure would enable re-establishment of its location for future identification.

A number of procedures and devices for marking and locating particular tissue locations are known in the prior art. For example, location wire guides, such as that described in U.S. Pat. No. 5,221,269 to Miller et al, are well known for locating lesions, particularly in the breast. The device described by Miller comprises a tubular introducer needle and an attached wire guide, which has at its distal end a helical coil configuration for locking into position about the targeted lesion. The needle is introduced into the breast and guided to the lesion site by an imaging system of a known type, for example, x-ray, ultrasound, or magnetic resonance imaging (MRI), at which time the helical coil at the distal end is deployed about the lesion. Then, the needle may be removed from the wire guide, which remains in a locked position distally about the lesion for guiding a surgeon down the wire to the lesion site during subsequent surgery. While such a location system is effective, it is obviously intended and designed to be only temporary, and is removed once the surgery or other procedure has been completed.

Other devices are known for marking external regions of a patient's skin. For example, U.S. Pat. No. 5,192,270 to Carswell, Jr. discloses a syringe which dispenses a colorant to give a visual indication on the surface of the skin of the point at which an injection has or will be given. Similarly, U.S. Pat. No. 5,147,307 to Gluck discloses a device which has patterning elements for impressing a temporary mark in a patient's skin, for guiding the location of an injection or the like. It is also known to tape or otherwise adhere a small metallic marker, e.g. a 3 millimeter diameter lead sphere, on the skin of a human breast in order to delineate the location of skin calcifications (see Homer et al, *The Geographic Cluster of Microcalcifications of the Breast, Surgery, Gynecology, & Obstetrics*, December 1985). Obviously, however, none of these approaches are useful for marking and delineating internal tissue abnormalities, such as lesions or tumors.

Still another approach for marking potential lesions and tumors of the breast is described in U.S. Pat. No. 4,080,959. In the described procedure, the skin of the portion of the body to be evaluated, such as the breasts, is coated with a heat sensitive color-responsive chemical, after which that portion of the body is heated with penetrating radiation such as diathermy. Then, the coated body portion is scanned for color changes which would indicate hot spots beneath the skin surface. These so-called hot spots may represent a tumor or lesion, which does not dissipate heat as rapidly because of its relatively poor blood circulation (about ½0 of the blood flow through normal body tissue). This method, of course, functions as a temporary diagnostic tool, rather than a permanent means for delineating the location of a tumor or lesion.

A method of identifying and treating abnormal neoplastic tissue or pathogens within the body is described in U.S. Pat. No. 4,649,151 to Dougherty et al. In this method, a tumor-selective photosensitizing drug is introduced into a patient's body, where it is cleared from normal tissue faster than it is cleared from abnormal tissue. After the drug has cleared normal tissue but before it has cleared abnormal neoplastic tissue, the abnormal neoplastic tissue may be located by the luminescence of the drug within the abnormal tissue. The fluorescence may be observed with low intensity light, some of which is within the drugs absorbance spectrum, or higher intensity light, a portion of which is not in the drugs absorbance spectrum. Once detected, the tissue may be destroyed by further application of higher intensity light having a frequency within the absorbance spectrum of the drug. Of course, this method also is only a temporary means for marking the abnormal tissue, since eventually the drug will clear from even the abnormal tissue. Additionally, once the abnormal tissue has been destroyed during treatment, the marker is destroyed as well.

It is also known to employ biocompatible dyes or stains to mark breast lesions. First, a syringe containing the colorant is guided to a detected lesion, using an imaging system. Later, during the extraction procedure, the surgeon harvests a tissue sample from the stained tissue. However, while such staining techniques can be effective, it is difficult to precisely localize the stain. Also, the stains are difficult to detect fluoroscopically and may not always be permanent.

Additionally, it is known to implant markers directly into a patients body using invasive surgical techniques. For example, during a coronary artery bypass graft (CABG), which of course constitutes open heart surgery, it is common practice to surgically apply one or more metallic rings to the aorta at the site of the graft. This enables a practitioner to later return to the site of the graft by identifying the rings, for evaluative purposes. It is also common practice to mark a surgical site with staples, vascular clips, and the like, for the purpose of future evaluation of the site.

A technique has been described for the study of pharyngeal swallowing in dogs, which involves permanently implanting steel marker beads in the submucosa of the pharynx (S. S. Kramer et al, *A Permanent Radiopaque Marker Technique for the Study of Pharyngeal Swallowing in Dogs, Dysphagia*, Vol. 1, pp. 163–167, 1987). The article posits that the radiographic study of these marker beads during swallowing, on many occasions over a substantial period of time, provides a better understanding of the pharyngeal phase of degluitition in humans. In the described technique, the beads were deposited using a metal needle cannula having an internal diameter slightly smaller than the beads to be implanted. When suction was applied to the cannula, the bead sat firmly on the tip. Once the ball-tipped cannula was inserted through tissue, the suction was broken, thereby releasing the bead, and the cannula withdrawn.

Of course, this technique was not adapted or intended to mark specific tissue sites, but rather to mark an entire region or structure of the body in order to evaluate anatomical movements (i.e. swallowing motions). It also was not intended for use in humans.

Accordingly, what is needed is a method and device for non-surgically implanting potentially permanent markers at the situs of a lesion or other abnormal tissue, for the purpose of defining the margins of a lesion before it is removed and/or to establish its location after it has been removed. The markers should be easy to deploy and easily detected using state of the art imaging techniques.

SUMMARY OF THE INVENTION

This invention solves the problems noted above by providing an implantable device which is particularly adapted to mark the location of a biopsy or surgery for the purpose of identification. The device is remotely delivered, preferably percutaneously. Visualization of the marker is readily accomplished using various state of the art imaging systems. Using the invention, it is possible to permanently mark the location or margins of a lesion or other tissue site, prior to removing or sampling same. The markers function to provide evidence of the location of the lesion after the procedure is completed, for reference during future examinations or procedures.

More particularly, a device is provided for marking tissue within a human body to identify a selected location for a diagnostic or therapeutic procedure. The device comprises a marker element and an apparatus for remotely delivering the marker element from outside the human body to the selected tissue location. Since, with remote delivery (e.g. percutaneously) direct visual access is not possible, an aided visualization device is used, such as an imaging system, an endoscope, or the like. Deployment of the marker element is such that it becomes implanted in the tissue.

The delivery apparatus preferably includes a member, which may comprise a tube, such as a needle, cannula, or trocar, of any known type for delivering medications, surgical equipment, or other items to the interior of a patient's body. The member may also be the body of an optical instrument such as an endoscope, laparoscope, or arthroscope. In the preferred embodiment, a biopsy needle or gun, such as is often used to extract tissue for examination in a biopsy procedure, is used in conjunction with the marking device, comprising a portion of the delivery apparatus, in order to provide a means for entering the patient's body and positioning the marker element at the selected tissue location. However, in other embodiments, the marking device is self contained, having a means itself for obtaining entry to the body, and being guided by a commercially available guidance system, such as a stereotactic guidance system.

The aforementioned member or tube, which typically comprises a cannula or needle having a lumen, has a distal end portion or region and a proximal end portion or region, and is adapted to extend through the body. The distal region is adapted to retain and deploy the marker element and the proximal region is linked to the distal region, so that predetermined marker deployment functions may be communicated from the proximal region to the distal region. In some embodiments, these deployment functions are communicated by means of the marker elements themselves travelling through the lumen for deployment from the distal region. In other embodiments, an actuator extends axially through the lumen to communicate deployment functions to the marker element held on or by the distal region. The apparatus is preferably guided to the selected tissue location, i.e. the site of the detected lesion or other abnormality, using a stereotactic guidance system or similar imaging system.

Several alternative embodiments of the marking device are disclosed. In one embodiment, the distal region of the tube includes a forming die, which is adapted to form each marker element into a predetermined shape, preferably a helix, as the marker element is deployed from the lumen. In a number of alternative embodiments, a mechanism, such as a mandrel, is used to push the marker elements through the tube. The marker elements may comprise a pre-formed spring having a predetermined shape, which is compressed into a linear position within the tube lumen. Upon deployment from the lumen, the spring is adapted to expand and assume its predetermined shape to such an extent that the energy of its expansion is sufficient to implant the marker element into the tissue at the selected tissue location. In some embodiments, implantation is accomplished because the marker elements have a plurality of attachment elements, each having a tip end (sometimes sharpened) which expands outwardly with sufficient energy to embed and anchor itself into the tissue at the selected tissue location. In other embodiments, the marker element has blunt, rather than sharpened edges, but is adapted to expand sufficiently upon exiting from the tube that its edges press radially against the selected tissue, thereby wedging and implanting the marker element.

In yet another embodiment of the invention, the tube lumen is adapted to receive a deployment actuator connector, or center wire, which extends axially through the lumen. The connector includes a distal portion which extends distally of the tube and a proximal portion which extends proximally of the tube. The proximal portion is attached to a deployment actuator, such as a pull ring, while the distal portion is attached to the marker element. On the connector, proximal to the distal portion, is a predetermined failure point which is adapted to be the weak point on the connector by failing first under tension. In operation, once the tube distal region has been positioned at the selected tissue location, the deployment actuator is actuated in a proximal direction to pull the marker element against the distal region of the tube. The tube distal region thus functions as a forming die to cause the marker element to bend until it abuts the tube distal region at its junction with the distal portion of the connector, such that the marker element is reconfigured to a desired shape. The proximal portion of the connector is adapted to be severed from the distal portion at the predetermined failure point upon the application of continued tension on the deployment actuator after abutment of the marker element against the tube distal region, thereby releasing and implanting the marker element.

Another important feature of the invention is the ability to utilize marker elements having a plurality of shapes. In some embodiments, these shapes may be created merely by utilizing different sized material stock or different cross sections. This shape diversity permits the adoption of a system wherein each shape denotes a different selected tissue location or event.

In a preferred embodiment of the invention, the device is adapted to be employed in combination with a medical instrument which transports the device to the selected tissue location responsive to positional control by a guidance system. The medical instrument preferably draws a vacuum to isolate and retain tissue at the selected location in a tissue receiving port. The marking device is adapted to deploy the marker element into the retained tissue.

In another aspect of the invention, a marker element is provided for marking tissue within a human body to identify a selected location for a diagnostic or therapeutic procedure. The marker element, which is preferably comprised of a biocompatible, implantable, and substantially radiopaque material, is adapted to be deployed to the selected tissue location percutaneously by a delivery instrument, so as to become implanted in the tissue.

A number of different marker element configurations and materials may be employed. Materials may include stainless steel, titanium, and the like, as well as non-metallic materials, such as polymers, salts, and ceramics, for example. In some embodiments, the marker element may actually be formed into a desired shape by a forming die in the delivery instrument, while in other embodiments, it may comprise a spring which radially expands upon exit from the delivery instrument to embed itself in the tissue.

In yet another aspect of the invention, a method for permanently marking tissue in a human body to identify a selected location for a diagnostic or therapeutic procedure is disclosed, which comprises actuating a delivery instrument, having a tube with a distal region, to a position wherein the tube extends through the human body and the distal region is at the selected location. A marker element is then deployed from the tube distal region to the selected tissue location so that it becomes anchored in the tissue.

These and other aspects and advantages of the present invention are set forth in the following detailed description and claims, particularly when considered in conjunction with the accompanying drawings in which like parts bear like reference numerals.

BRIEF DESCRIPTION OF THE DRAWING

FIG. 1 is a cross-sectional view of a biopsy instrument embodiment as described in co-pending patent application Ser. No. 08/217,246 now U.S. Pat. No. 5,526,822, configured to be utilized as a preferred instrument for use in conjunction with the inventive tissue marking device;

FIGS. 2 and 3 are cross-sectional views illustrating the sequential steps in the operation of the biopsy instrument embodiment needed to capture tissue targeted for marking;

FIG. 4 is a cross-sectional view of one embodiment of a tissue marking device constructed in accordance with the principles of the invention, illustrating the device in a first position in preparation for delivering a marker to tissue targeted for marking;

FIGS. 5, 6, 7, and 8 are cross-sectional views similar to FIG. 4, illustrating sequentially the delivery of a marker to the targeted tissue;

DETAILED DESCRIPTION OF THE INVENTION

Figure 9:
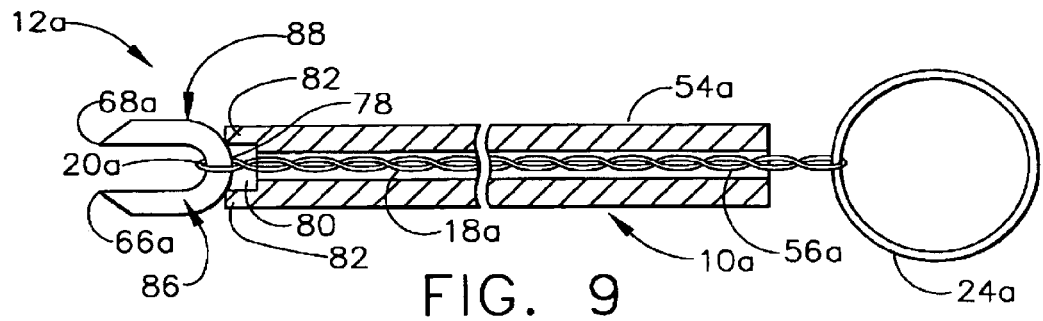
FIGS. 9, 10, and 11 are schematic cross-sectional views of an alternative embodiment of a tissue marking device constructed in accordance with the principles of the invention, illustrating sequentially the delivery of a marker to the targeted tissue.

Now with more particular reference to the drawings, FIGS. 4–8 illustrate sequentially the deposit of a marker into a desired tissue location, utilizing a preferred embodiment of the invention. Specifically, the marking instrument 10 comprises a marker element 12 which includes an umbrella end comprising a pair of attachment members or wings 14 and 16, and a center wire 18. All three wires 14, 16 and 18 are joined at the distal end 20 of the center wire 18, preferably by welding. At the proximal end 22 of the center wire is a deployment actuator or pull ring 24, which is preferably attached by welding or brazing.

To place the marker element 12 at a desired location, a biopsy needle or gun is preferably used, though other known delivery means could be used as well. For example, the stand-mounted biopsy instrument described in U.S. patent application Ser. No. 08/217,246, previously incorporated by reference into this application, is a preferred instrument for introducing the marker element into the body of a patient. One embodiment of such an instrument 26 is partially illustrated in FIGS. 1–3. The biopsy instrument 26 includes a housing 28. A hollow outer piercing needle 38 is attached to the housing 28 at location 34. A distal end of the hollow outer piercing needle 38 includes a point 40. Hollow outer piercing needle 38 also includes a tissue receiving port or bowl 42 (FIGS. 2 and 3). A cannular inner cutter 44 is movably positioned coaxially within the hollow outer piercing needle 38 and housing 28. A vacuum line 46 supplies vacuum to ports 50 in the bottom of the receiving bowl 42.

Operation of the biopsy instrument to facilitate the placement of a tissue marker is illustrated sequentially in FIGS. 1–3. FIG. 1 illustrates the distal end point 40 of the hollow outer piercing needle 38 in position to pierce a target tissue 51. The initial position of the point 40 with respect to the tissue area being marked is determined by the overall position of the biopsy instrument with respect to the patient. For example, the entire biopsy instrument may be mounted on a commercially available stereotactic guidance system (not shown) commonly used in the medical field for accurate positioning of a variety of medical devices with respect to a patient. A detailed description of such a motorized biopsy needle positioner, i.e. stereotactic guidance system, is given in U.S. Pat. No. 5,240,011, issued on Aug. 31, 1993 to Michael Assa, which is hereby incorporated herein by reference. The suspect lesion within tissue 51 is to be targeted and marked according to the instructions provided with the stereotactic guidance system. As shown in FIG. 1, the stereotactic guidance system has positioned the biopsy instrument 26 such that the distal end point 40 is immediately adjacent to the surface of the tissue 51. Once the point 40 is adjacent the specific lesion to be marked, the needle 38 is fired into the lesion such that the point 40 traverses through the lesion, thereby placing the tissue receiving bowl 42 in the center of the lesion.

As shown in FIG. 2, after the hollow outer piercing needle 38 has been positioned at the precise location within the tissue 51 at which it is desired to mark tissue, the cutter 44 is moved proximally of the housing 28 to provide an entry access for the tissue marker delivery system.

As shown in FIG. 3, a vacuum source attached to vacuum line 46 is actuated, thereby generating a region of low pressure at the vacuum ports 50 to facilitate the prolapse of tissue 51a immediately adjacent to the tissue receiving port 42 into the hollow interior of hollow outer piercing needle 38.

Now again referring to FIGS. 4–8, the marking instrument 10 includes a tube 54. The center wire 18 runs axially through a lumen 56 of the tube 54, with the pull ring 24 being attached to the proximal end of the center wire 18, proximally of the tube 54. The distal end 20 of the center wire extends distally of the tube 54 and is joined to attachment members 14 and 16, as described above.

In operation, the tube 54 of the marking instrument is inserted into the patient's body in the direction of the arrow 58, as shown in FIG. 4, until the distal end 20 of the center wire 18 approaches the desired location, adjacent to or in the abnormal tissue or lesion. Because direct visual access to the targeted tissue is impossible, an aided visualization device, such as the stereotactic guidance system described above, is used to guide the distal portion of the marking instrument to the targeted tissue. Then, if the biopsy instrument shown in FIGS. 1–3 is utilized to deploy the markers, the targeted tissue 51a (FIG. 5) is vacuumed into the tissue receiving port 42. Referring particularly to FIG. 5, once the distal end 20 of the center wire reaches the targeted, vacuumed tissue, the ring 24 is pulled away from the tissue in the direction of the arrow 60. This action deploys the marker attachment members 14 and 16 as they are forced into a die formed in the tip 62 of the tube. This die may take any desired form, depending upon the desired deployed configuration of the attachment members 14, 16.

With reference to FIG. 6, tension continues to be applied to the ring 24, in the direction shown by the arrow 64, until the distal end of the marker is fully deployed. Forcing the attachment members into the die 62 causes them to extend outwardly, as illustrated, into the tissue. Their outward energy anchors the marker element 12 in the tissue for permanent implantation. The tips 66 and 68 of the attachment members may be configured to be less traumatic as an implant, or may alternatively be sharpened to provide a more secure grip. At full deployment, the width of the umbrella end of the marker element is preferably about 0.035 to 0.045 inches, though other sizes may be utilized within the scope of the invention.

Now referring to FIG. 7, even after the attachment members 14 and 16 have been fully deployed, the pull ring 24 is pulled to further increase tension in the direction of the arrow 70, until the center wire 18 is sheared at a point of weakness or detent 72 (see FIGS. 4–6) which is established in the center wire 18 proximally of the tip 20. Once failure has occurred, the pull ring 24 and the proximal portion 18' of the center wire may be discarded as they are severed from the marker element 12 and remaining distal portion 18" of the center wire.

Finally, with reference to FIG. 8, to finish placing the marker element 12, the tube 54 is withdrawn in the direction of the arrow 74, as illustrated. The marker element is thereby permanently secured to locate the lesion site for future examination by known imaging methods.

In the preferred embodiment, the marker element 12 is fabricated of stainless steel. However, many other biocompatible, radiopaque, implantable materials may be used for the marker element 12 as well, including, for example, titanium, tantalum, or nickel-titanium alloys. Additionally, while a 3-pronged umbrella end is shown and described, any number of prongs may be used, if desired.

While it is preferred that the marker element 12 be deployed using the biopsy instrument described and shown in FIGS. 1–3, any instrument capable of delivering the element percutaneously may be utilized. Such instruments, for example, may include the hand-held biopsy gun described in U.S. Pat. No. Re. 34,056, entitled "TISSUE SAMPLING DEVICE" and issued to Lindgren et al. All of these types of instruments include a tube (typically a cannula or needle) which is adapted to enter the body, and would be capable of delivering the marker element. It is also within the scope of the invention to deliver the marker element through any tube which has access to the body or using optical medical instruments, such as endoscopes, arthroscopes, or laparoscopes, in which case the marker element is delivered to the desired tissue site from outside the body of the patient, through the body of the instrument.

Figure 10:
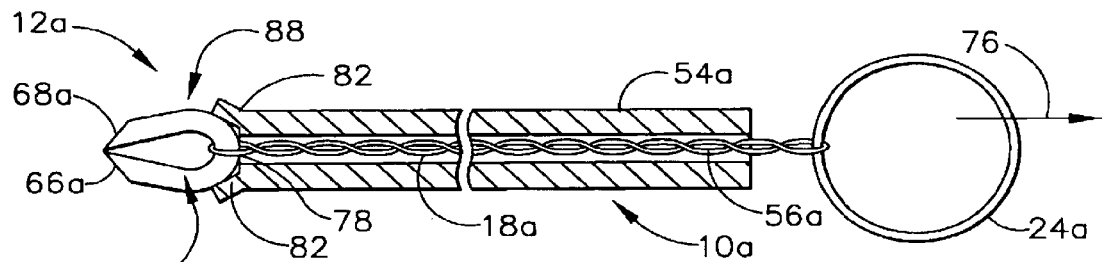
Figure 11:
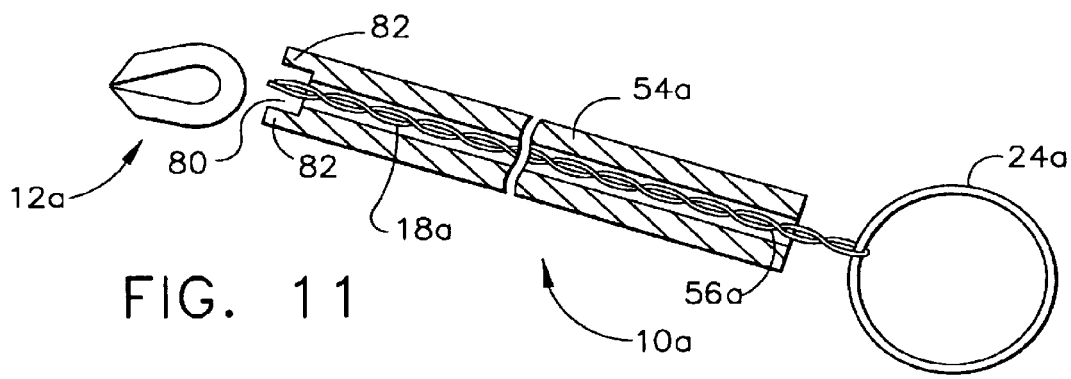

Now with reference to FIGS. 9–11, an alternative embodiment of a marking instrument 10*a* is shown, which is identical to the instrument 10 in all respects not shown or described herein. Portions of the instrument 10*a* corresponding to portions of the instrument 10 are designated by corresponding reference numerals followed by the letter a.

The FIG. 9 embodiment is substantially similar to the FIG. 4 embodiment, in that the marking instrument includes a tube 54*a* which has a lumen 56*a*, and may utilize a cannula, needle, or imaging instrument (i.e. endoscope, laparoscope, or the like) for access to a delivery site within the body and to aid in delivery. Again, as is the case for all succeeding embodiments, it is preferred that the tube 54*a* utilize the hollow outer piercing needle 38 of the biopsy instrument shown in FIGS. 1–8, though any other instrument which is capable of delivering a marker percutaneously or through a body orifice from a location outside the patient's body may be utilized. A center wire 18*a* runs longitudinally through the lumen 56*a*. At the proximal end of the center wire 18*a* is a deployment actuator or pull ring 24*a*. At the distal end of the center wire is the marker element 12*a*.

A primary difference between the FIG. 4 and FIG. 9 embodiments is that the FIG. 9 marker element 12*a* is preferably a generally "U" shaped element resembling a surgical ligating clip, having tips 66*a* and 68*a*, which is captured by the distal looped end 20*a* of the twisted center wire. In operation, once the tips 66*a* and 68*a* of the marking element 12*a* reach the targeted tissue, the ring 24*a* is pulled rightwardly in the direction of the arrow 76 (FIG. 10). This action retracts the base portion 78 of the marker element 12*a* into a forming recess 80 (FIG. 9), wherein the recessed tube wall 82 forces prongs 86 and 88 together until tips 66*a* and 68*a* of the prongs 86 and 88, respectively, contact or nearly contact one another (FIG. 10). At this point, increasing tension applied to the pull ring 24*a* causes the wire 18*a* to fail at a point of weakness or detent (not shown) provided in the center wire at or near its tip end 20*a*, thereby releasing the marker into the target tissue, as illustrated in FIG. 11.

Figure 12:
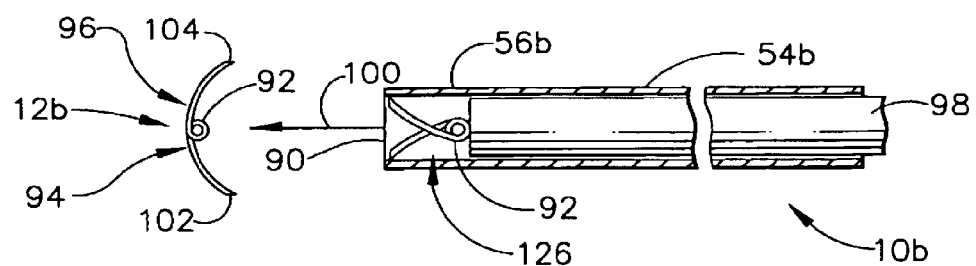
FIG. 12 is a schematic cross-sectional view illustrating a third alternative embodiment of a tissue marking device constructed in accordance with the principles of the invention.

Referring now to FIG. 12, a second alternative embodiment of a marking instrument 10*b* is shown, which is identical to the instrument 10 in all respects not shown or described herein. Portions of the instrument 10*b* corresponding to portions of the instrument 10 are designated by corresponding reference numerals followed by the letter b.

The FIG. 12 embodiment is substantially similar to the FIG. 4 embodiment, in that the marking instrument includes a tube 54*b* which has a lumen 56*b*, and may utilize a cannula, needle, or imaging instrument (i.e. endoscope, laparoscope, or the like) for access to delivery site within the body and to aid in delivery.

There are two primary differences between the embodiments of FIGS. 4 & 9 and that of FIG. 12. First, in the FIG. 12 embodiment, a plurality of marker elements 12*b* (two are shown, though any number may be employed) may be preloaded into the tube 54*b*, each comprising a preformed spring which is deployed through the tube's distal region 90 in an axial direction. Second, the nature of the deployment mechanism utilizes a compressive rather than tensile force. It may further be noted that, though end deployment of the marker elements in the FIG. 12 embodiment is illustrated, they may be similarly deployed radially through a side port (not shown) in tube 54*b*, or at any other angle, to accommodate delivery through an existing instrument (i.e. cannula, needle, endoscope, laparoscope, or the like). In being deployed radially, the distal region 90 is not used for passage of the marker element and could be utilized to house a piercing element (not shown) similar to that shown in FIGS. 1–3. Armed with the piercing element, this marker delivery system would not be dependent on a positioning system as described in FIGS. 1–3 for placement at the tissue site and could be used alone in conjunction with a commercially available stereotactic or other guidance system. This concept may be applied to all subsequent embodiments except that illustrated in FIG. 16.

Still with reference to FIG. 12, each marker element or spring 12*b* preferably includes a center coil 92 from which a pair of attachment members 94 and 96 extend, and is adapted to automatically attach itself to the target tissue by utilizing its own stored energy. Thus, in operation, each spring 12*b* is held in a compressed position within the tube 54*b*. When it is desired to deploy the marker, a mandrel 98 is preferably utilized to push the spring 12*b* through the center lumen 56*b* and out through the distal open end 90 of the tube. Once the spring exits the tube, stored energy causes the attachment members 94 and 96 to expand outwardly, as shown. As this expansion occurs, the tips 102 and 104 of the attachment members 94 and 96, respectively, anchor themselves into the tissue to permanently secure the marker element in the desired location. As with the FIG. 4 embodiment, the tips 102 and 104 may be blunt to be less traumatic as an implant, or may alternatively be sharpened or barbed to provide a more secure grip. Once a spring has been deployed, the instrument may be repositioned to the next desired location for the immediate deployment of another marker until the supply in the tube 54*b* is exhausted, eliminating the need to remove and re-load the marking instrument 10*b* between each deployment.

Again in this embodiment, the spring 12*b* may be fabricated of any known biocompatible, implantable, radiopaque material, though stainless steel is preferred. Additionally, the forces required to deploy the attachment members on the spring may be customize by varying the spring filar, dimensions, material, and/or the number of coils in the torsional part of the spring.

Figure 13:
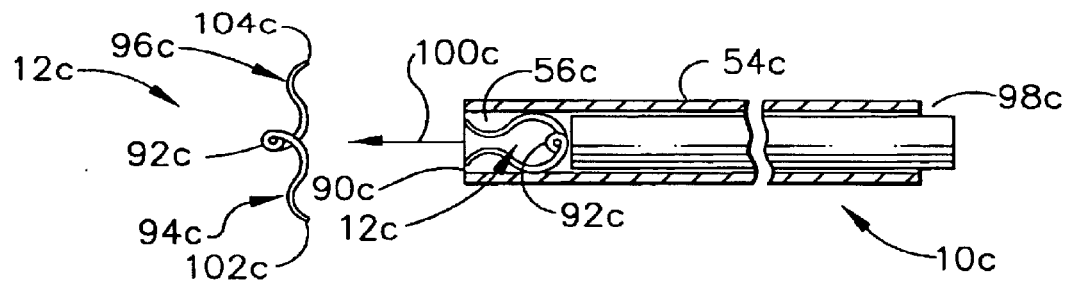
FIG. 13 is a schematic cross-sectional view illustrating a fourth alternative embodiment of a tissue marking device constructed in accordance with the principles of the invention.

FIG. 13 illustrates another alternative embodiment of the marking instrument 10, which is identical to the instrument 10*b* of FIG. 12 in all respects not shown or described herein. Portions of the instrument 10*c* corresponding to portions of the instrument 10*b* of FIG. 12 are designated by corresponding reference numerals followed by the letter c.

In actuality, the FIG. 13 embodiment is substantially identical to that of FIG. 12, except for the shape of each spring 12c, and is employed in precisely the same manner. Thus, to deploy a marker element 12c, the mandrel 98c is utilized to push the spring 12c through the center lumen 56c and out through the distal open end 90c of the tube. As in the FIG. 12 embodiment, the marker element travels in the direction of the arrow 100c, until the attachment members 94c and 96c extend outwardly sufficiently to anchor themselves to the target tissue. Also, the FIG. 13 embodiment is similar to the FIG. 12 embodiment in that the instrument may be re-positioned to immediately deploy another marker element without re-loading, and marker elements may be deployed radially through a side port in tube 54c (not shown), or any other angle, to accommodate delivery through an existing instrument (i.e. cannula, needle, endoscope, laparoscope, or the like).

Figure 14:
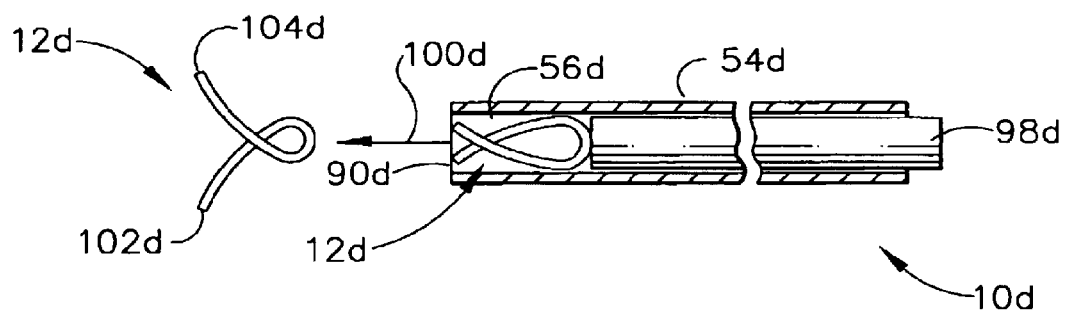
FIG. 14 is a schematic cross-sectional view illustrating a fifth alternative embodiment of a tissue marking device constructed in accordance with the principles of the invention.

FIG. 14 shows still another alternative embodiment of the marking instrument 10, which is also substantially identical to the instrument 10b of FIG. 12 in all respects not shown or described herein. Portions of the instrument 10d corresponding to portions of the instrument 10b of FIG. 12 are designated by corresponding reference numerals followed by the letter d.

Again, the FIG. 14 embodiment is substantially identical to those of FIGS. 12 and 13, except for the shape of the marker element or spring 12d. A marker element 12d is deployed preferably using a mandrel 98d or the like to push the spring 12d through the center lumen 56d until it exits through the open end 90d of the tube. As in the FIGS. 12 and 13 embodiments, the marker element travels in the direction of the arrow 100d, until the tips 102d and 104d extend outwardly sufficiently to anchor themselves to the target tissue.

In practice, a radiologist or other operator of the equipment can use a marker shaped like marker 12b, as shown in FIG. 12, during one biopsy, then use a differently shaped marker, such as the marker 12c in the FIG. 13 embodiment, or the marker 12d in the FIG. 14 embodiment, during a subsequent biopsy procedure. The differently shaped markers permit the distinction between different biopsy procedures during future imaging procedures, as well as between biopsy sites which may be close in proximity, thereby improving the information available to the radiologist and thus the ability to monitor or diagnose the patient's future condition more precisely.

Figure 15:
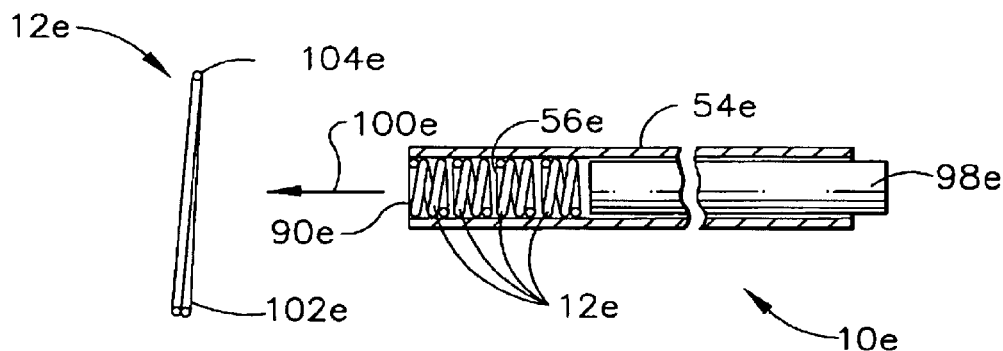
FIG. 15 is a schematic cross-sectional view illustrating a sixth alternative embodiment of a tissue marking device constructed in accordance with the principles of the invention.

FIG. 15 illustrates yet another alternative embodiment of the marking instrument 10, which is also substantially identical to the instrument 10b of FIG. 12 in all respects not shown or described herein. Portions of the instrument 10e corresponding to portions of the instrument 10b of FIG. 12 are designated by corresponding reference numerals followed by the letter e.

In this embodiment, each marker element 12e is deployed distally through the open distal region 90e of the tube 54e by a mandrel 98e, much as in the previous embodiments shown in FIGS. 12, 13, and 14. The primary difference, however, between this embodiment and the previous embodiments is that, while the marker elements in the previous embodiments rely largely on the barbed nature of the spring to secure themselves in the tissue, in this embodiment, the springs are secured simply because of their significant expansion upon exit from the tube. This embodiment particularly lends itself to marking the boundaries of a biopsy or other desired site by defining the perimeter of the site. The expansion of the spring 12e causes the blunt edges 102e and 104e to press outwardly against the selected tissue, thereby wedging the spring securely into position.

An advantage of this embodiment is that, because of the tight compression of the springs 12e within the tube 54e, a larger number of markers can be inserted therein simultaneously, thereby permitting the deployment of more markers without having to pause and disengage to re-load.

Another advantage the FIG. 15 embodiment provides is the ability to deploy springs adapted to expand to a number of different sizes all from the same lumen. Larger sized springs would require more coils within a given lumen than smaller sized springs (not shown).

It should be noted that the springs need not be limited to the configuration illustrated, but could include any spring of any configuration which expands to secure its position. While stainless steel is presently preferred, any other biocompatible, implantable, and radiopaque material could be used alternatively. Also as in the previous embodiments, marker elements may be similarly deployed radially through a side port in tube 54e (not shown), or any other angle, to accommodate delivery through an existing instrument (i.e. cannula, needle, endoscope, laparoscope, or the like).

Figure 16:
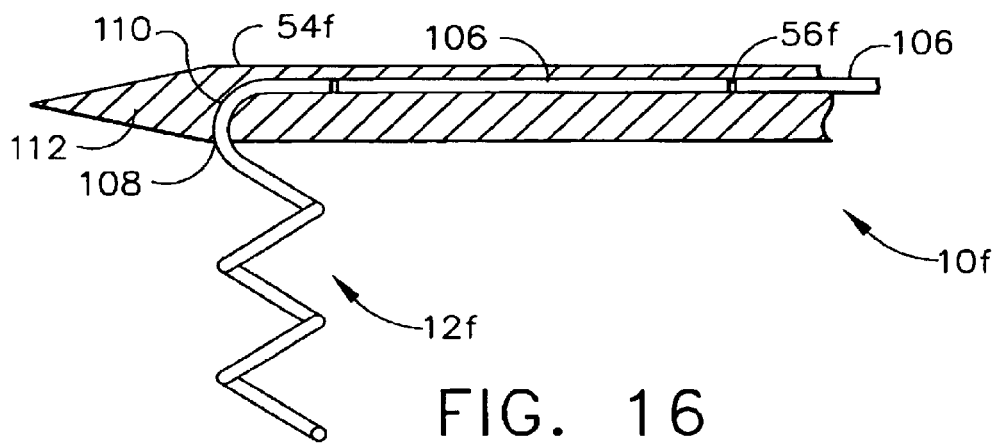
FIG. 16 is a schematic cross-sectional view illustrating a seventh alternative embodiment of a tissue marking device constructed in accordance with the principles of the invention.

Still another alternative embodiment of the marking instrument 10 is shown in FIG. 16. In this embodiment, the marking instrument 10f comprises a tube 54f. Wire segments 106 of any desired length are preloaded into the lumen 56f, which runs along substantially the entire length of the tube 54f. Once the needle is properly positioned, the marker elements 12f are deployed by pushing them out of the tip of the needle, through the side exit port 108. A curved portion 110 of the lumen 56f comprises a die portion, and is adapted to form the wire segments 106 into helical marker elements 12f as they pass therethrough, pushed by a mandrel (not shown) or other known means from the tip of the needle through the exit port 108. The nature of the curve or curves in the die portion 110 and preformed curves imparted into the wire segments determine the final shape (which resembles a partial or whole helix) and dimensions of the marker element.

This embodiment is versatile in that it is capable of continuously deploying any number of marker elements without the necessity of re-loading, since all that is required is a continuous feed of wire segments into the proximal region of the tube 54f. Furthermore, differently sized and shaped helixes may be delivered in the same procedure by utilizing marker wires of different diameters and/or preformed curves, which approximate different helical shapes as they pass through the die portion. Thus, loading a plurality of different sized wires into the needle yields a plurality of different shaped markers.

Of course, as with the previous embodiments, although stainless steel is presently preferred, many different types of biocompatible, implantable, and radiopaque materials could be utilized within the scope of the invention. Also as in the previous embodiments, marker elements may be similarly deployed at different angles to accommodate delivery through an existing instrument (i.e. cannula, needle, endoscope, laparoscope, or the like).

Unlike previous embodiments, FIG. 16 preferably incorporates a piercing element 112 enabling this marker to be delivered without the aid of the positioning system described in FIGS. 1–3 for placement at the tissue site. This embodiment could be used alone in conjunction with a commercially available stereotactic or other (i.e. ultrasonic) guidance system.

Figure 17:
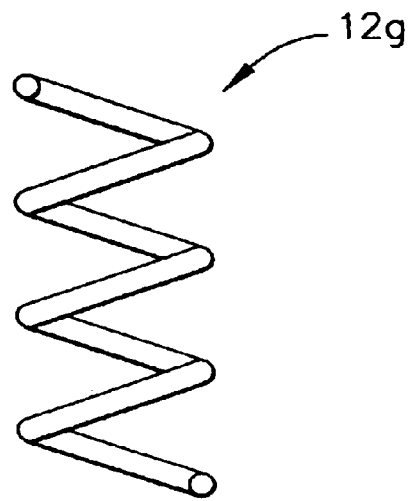
FIG. 17 is a front elevation view of an alternative marker element embodiment.

Though a number of different embodiments of the conceptual invention have been described and shown, it is considered to be within the scope of the invention for the marking elements and delivery instruments to take on many other forms. For example, embolization coils like that illustrated in FIG. 17 and designated with reference numeral 12g are well known in the medical field for placement into vessels such as veins and arteries in order to block off fluid flow abnormalities (such as fistulas and arteriovenous malformations). These coils have been made of various materials, including stainless steel, platinum, and gold, and are wound into configuration similar to that of a light bulb filament. They are generally placed into the body using a catheter or trocar system. The inventors in the present application have discovered that such coils may indeed also be used as marker elements, for permanent implantation in target tissue, in a manner similar to that described previously with respect to FIGS. 1–16.

Figure 18:
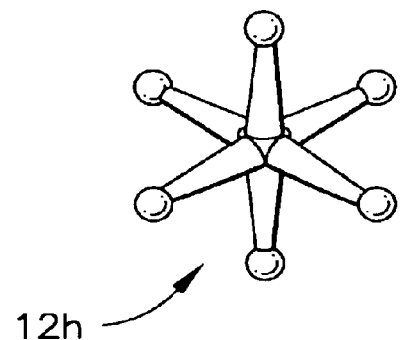
FIG. 18 is a perspective view of another alternative marker element embodiment.
Figure 19:
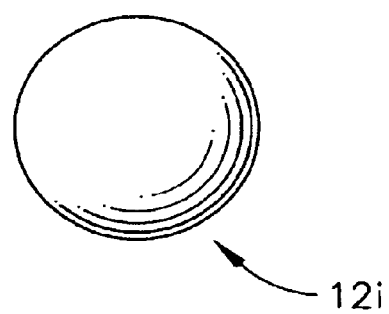
FIG. 19 is a front elevation view of yet another alternative marker element embodiment.

Marker elements of many other materials and configurations may be used as well. For example, one such multi-appendaged jack-shaped marker 12h is illustrated in FIG. 18. Additionally, small beads 12i (FIG. 19) of calcium carbonate or other radiodense materials, which are highly visible by mammographic imaging, could be deployed as marker elements. One such application would be to place a plurality of such beads or pellets (each having a diameter of about 500μ) around the entirety of a breast lesion prior to the extraction procedure, which would then serve as guides to ensure that all of the margins had been removed. During subsequent imaging procedures, they would function to denote the location of the previous biopsy for reference purposes.

Figure 20:
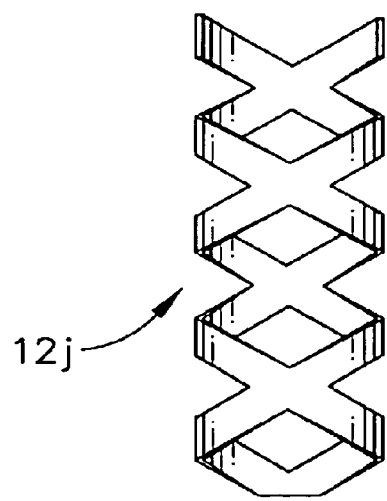
FIG. 20 is a front elevation view of still another alternative marker element embodiment.

Referring now to FIG. 20, yet another alternative marker element 12j, which is of a woven construction, is illustrated. Other such marker materials may include adhesives and epoxies which would be injected at the biopsy site. Biodegradable polymers and other plastics could also be used, as long as they are biocompatible, implantable, and visible using an imaging system.

While this invention has been described with respect to various specific examples and embodiments, it is to be understood that the invention is not limited thereto and that it can be variously practiced within the scope of the following claims.

What is claimed is:

1. A marker instrument comprising:
   a cube comprising:
      a lumen;
      an axial opening at a proximal end of said tube;
      a closed tip at a distal end of said tube;
      a side exit port proximal to said closed tip; and
   a plurality of marker elements disposed in said lumen;
   wherein said plurality of marker elements includes at least one radiopaque marker element, and wherein at least one marker has a shape different from that of at least one other marker.

2. A marker instrument, according to claim 1 wherein at least one marker comprises a metal.

3. A marker instrument according to claim 1 wherein at least one marker comprises non-metallic material.

4. A marker instrument according to claim 1 wherein at least one marker has a size different from that of at least one other marker.

5. A device for deploying a tissue marker at a biopsy site, the device comprising:
   a lube comprising:
      a lumen; and
      a side exit port communicating with said lumen;
   a plurality of tissue markers disposed in said lumen proximal of said side exit port;
   an element slidably disposed in said lumen for pushing said markers distally in said lumen for deployment of said markers through said side exit port;
   wherein at least one of said markers is visible using an imaging system, and wherein at least one marker has a size different from that of at least one other marker.

6. The device of claim 5 wherein at least one of said markers is radiopaque.

7. The device of claim 5 wherein the device is adapted to be inserted through an outer piercing needle of a biopsy instrument.

8. The device of claim 5 wherein at least one of said markers comprises stainless steel.

9. The device of claim 5 wherein said tissue markers are disposed end to end in said lumen.

10. The device of claim 5 wherein at least one marker has a shape different from that of at least one other marker.

11. The device of claim 5 wherein said markers are disposed in said lumen such that said markers are deployed one at a time.

12. The device of claim 5 wherein at least one marker comprises a metal.

13. The device of claim 5 wherein at least one marker comprises a non-metallic material.

14. A device for deploying a tissue marker at a biopsy site, the device comprising:
   a tube comprising:
      a lumen;
      a side exit port communicating with said lumen;
   a plurality of discrete tissue markers disposed in said lumen, wherein at least one marker has a size different from that of at least one other marker; and
   an element disposed in said lumen for pushing said markers distally in said lumen for deployment of said markers through said side exit port.

15. A device for deploying a tissue marker at a biopsy site, the device comprising:
   a tube comprising:
      a lumen;
      a side exit port communicating with said lumen;
   a plurality of discrete tissue markers disposed in said lumen, wherein at least one marker has a shape different from that of at least one other marker; and
   an element disposed in said lumen for pushing said markers distally in said lumen for deployment of said markers through said side exit port.

* * * * *

(12) EX PARTE REEXAMINATION CERTIFICATE (6145th)
United States Patent
Foerster et al.

(10) Number: US 7,044,957 C1
(45) Certificate Issued: Mar. 4, 2008

(54) DEVICES FOR DEFINING AND MARKING TISSUE

(75) Inventors: Seth A. Foerster, San Clemente, CA (US); Fred H. Burbank, San Juan Capistrano, CA (US); Mark A. Ritchart, Murrieta, CA (US); Elias A. Zerhouni, Baltimore, MD (US)

(73) Assignee: Ethicon Endo-Surgery, Cincinnatie, OH (US)

Reexamination Request:
No. 90/008,092, Jun. 9, 2006

Reexamination Certificate for:
Patent No.: 7,044,957
Issued: May 16, 2006
Appl. No.: 09/776,125
Filed: Feb. 2, 2001

Related U.S. Application Data

(63) Continuation of application No. 08/858,389, filed on May 19, 1997, now Pat. No. 6,228,055, which is a continuation of application No. 08/308,097, filed on Sep. 16, 1994, now abandoned.

(51) Int. Cl.
*A61B 17/34* (2006.01)

(52) U.S. Cl. .................................................. 606/185
(58) Field of Classification Search ................... 604/15, 604/57, 59–64, 502, 506
See application file for complete search history.

(56) References Cited

U.S. PATENT DOCUMENTS

| 3,351,049 A | 11/1967 | Lawrence |
| 4,900,304 A | 2/1990 | Fujioka et al. |
| 4,994,013 A | 2/1991 | Suthanthiran et al. |

*Primary Examiner*—David O. Reip

(57) ABSTRACT

In order to later identify the location of a biopsy or surgery, various means and methods for permanently and non-surgically marking selected tissue in the human body are used. Later visualization of the markers is readily accomplished using state-of-the-art imaging systems.

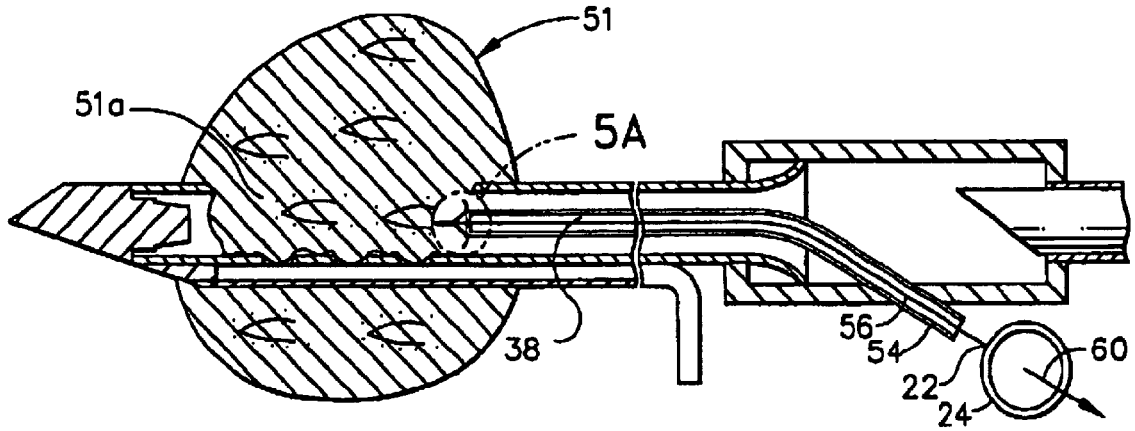

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claim(s) 1–15 is confirmed.

* * * * *

(12) EX PARTE REEXAMINATION CERTIFICATE (7047th)
United States Patent
Foerster et al.

(10) Number: US 7,044,957 C2
(45) Certificate Issued: Sep. 1, 2009

(54) DEVICES FOR DEFINING AND MARKING TISSUE

(75) Inventors: Seth A. Foerster, San Clemente, CA (US); Fred H. Burbank, San Juan Capistrano, CA (US); Mark A. Ritchart, Murrieta, CA (US); Elias A. Zerhouni, Baltimore, MD (US)

(73) Assignee: Ethicon Endo-Surgery, Cincinnati, OH (US)

Reexamination Request:
No. 90/009,100, Apr. 2, 2008

Reexamination Certificate for:
Patent No.: 7,044,957
Issued: May 16, 2006
Appl. No.: 09/776,125
Filed: Feb. 2, 2001

Reexamination Certificate C1 7,044,957 issued Mar. 4, 2008

Related U.S. Application Data

(63) Continuation of application No. 08/858,389, filed on May 19, 1997, now Pat. No. 6,228,055, which is a continuation of application No. 08/308,097, filed on Sep. 16, 1994, now abandoned.

(51) Int. Cl.
*A61B 17/34* (2006.01)

(52) U.S. Cl. .......................................................... 606/185
(58) Field of Classification Search ........................ None
See application file for complete search history.

(56) References Cited

U.S. PATENT DOCUMENTS

| | | | |
|---|---|---|---|
| 3,194,239 A | * | 7/1965 | Sullivan ..................... 606/228 |
| 4,832,686 A | | 5/1989 | Anderson |
| 4,900,304 A | | 2/1990 | Fujioka et al. |
| 5,353,804 A | | 10/1994 | Kornberg et al. |
| 5,562,613 A | | 10/1996 | Kaldany |

* cited by examiner

*Primary Examiner*—Cary E. O'Connor

(57) ABSTRACT

In order to later identify the location of a biopsy or surgery, various means and methods for permanently and non-surgically marking selected tissue in the human body are used. Later visualization of the markers is readily accomplished using state-of-the-art imaging systems.

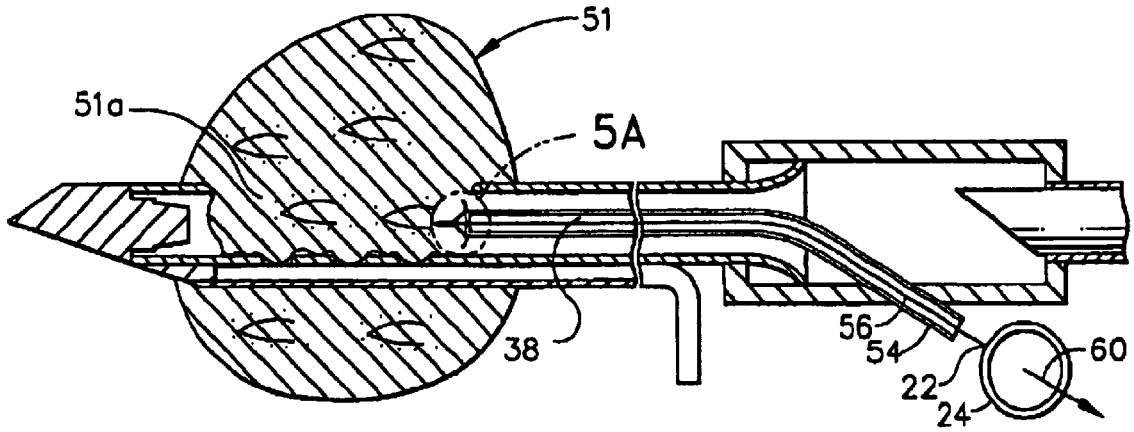

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 14 and 15 is confirmed.

Claims 1 and 5 are determined to be patentable as amended.

Claims 2–4 and 6–13, dependent on an amended claim, are determined to be patentable.

New claims 16–20 are added and determined to be patentable.

1. A marker instrument comprising:
   a [cube] *tube* comprising:
      a lumen;
      an axial opening at a proximal end of said tube;
      a closed tip at a distal end of said tube;
      a side exit port proximal to said closed tip; and
   a plurality of marker elements disposed in said lumen;
   wherein said plurality of marker elements includes at least one radiopaque marker element, and wherein at least one marker has a shape different from that of at least one other marker.

5. A device for deploying a tissue marker at a biopsy site, the device comprising:
   a [lube] *tube* comprising:
      a lumen; and
      a side exit port communicating with said lumen;
   a plurality of tissue markers disposed in said lumen proximal of said side exit port;
   an element slidably disposed in said lumen for pushing said markers distally in said lumen for deployment of said markers through said side exit port;
   where at least one of said markers is visible using an imaging system, and wherein at least one marker has a size different than that of at least one other marker.

*16. The device of claim 1 wherein said markers elements are disposed end to end in said lumen.*

*17. The marker instrument of claim 1 wherein at least one marker element has a cross-section different from at least one other marker element cross-section.*

*18. The marker instrument of claim 1 wherein at least one marker element is compressed within the tube.*

*19. The marker instrument of claim 1 wherein at least one marker element comprises a woven configuration.*

*20. The marker instrument of claim 1 comprising at least one bead-shaped or pellet shaped marker element.*

* * * * *